(12) United States Patent
Parramon et al.

(10) Patent No.: US 8,706,238 B2
(45) Date of Patent: Apr. 22, 2014

(54) CURRENT GENERATION ARCHITECTURE FOR AN IMPLANTABLE STIMULATOR DEVICE HAVING COARSE AND FINE CURRENT CONTROL

(75) Inventors: Jordi Parramon, Valencia, CA (US); David K. L. Peterson, Saugus, CA (US); Paul J. Griffith, Moorpark, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 343 days.

(21) Appl. No.: 12/838,260

(22) Filed: Jul. 16, 2010

(65) Prior Publication Data
US 2010/0286749 A1 Nov. 11, 2010

Related U.S. Application Data

(63) Continuation of application No. 11/550,763, filed on Oct. 18, 2006, which is a continuation-in-part of application No. 11/177,503, filed on Jul. 8, 2005.

(51) Int. Cl.
*A61N 1/02* (2006.01)
(52) U.S. Cl.
USPC ............................................. 607/46
(58) Field of Classification Search
USPC ................................. 607/45, 57, 64
See application file for complete search history.

(56) References Cited

U.S. PATENT DOCUMENTS

| | | | |
|---|---|---|---|
| 3,646,940 A | 3/1972 | Timm et al. | |
| 3,724,467 A | 4/1973 | Avery et al. | |
| 3,822,708 A | 7/1974 | Zilber | |
| 5,522,865 A | 6/1996 | Schulman et al. | |
| 5,603,726 A | 2/1997 | Schulman et al. | |
| 6,181,969 B1 | 1/2001 | Gord | |
| 6,301,505 B1 | 10/2001 | Money | |
| 6,381,496 B1 | 4/2002 | Meadows et al. | |
| 6,516,227 B1 | 2/2003 | Meadows et al. | |
| 6,690,974 B2 | 2/2004 | Archer et al. | |
| 7,532,936 B2 | 5/2009 | Erickson et al. | |
| 7,539,538 B2 | 5/2009 | Parramon et al. | |
| 2010/0042187 A1 | 2/2010 | Werder et al. | |

FOREIGN PATENT DOCUMENTS

| WO | 00/76436 | 12/2000 |
|---|---|---|
| WO | 2005/101627 | 10/2005 |

OTHER PUBLICATIONS

Notice Regarding Copying Claims (filed herewith), Jul. 16, 2010.

*Primary Examiner* — Joseph Dietrich
(74) *Attorney, Agent, or Firm* — Wong, Cabello, Lutsch, Rutherford & Brucculeri, LLP.

(57) ABSTRACT

Disclosed herein is a current generation architecture for an implantable stimulator device such as an Implantable Pulse Generator (IPG). Current source and sink circuitry are both divided into coarse and fine portions, which respectively can provide a coarse and fine current resolution to a specified electrode on the IPG. The coarse portion is distributed across all of the electrodes and so can source or sink current to any of the electrodes. The coarse portion is divided into a plurality of stages, each of which is capable via an associated switch bank of sourcing or sinking a coarse amount of current to or from any one of the electrodes on the device. The fine portion of the current generation circuit preferably includes source and sink circuitry dedicated to each of the electrode on the device, which can comprise digital-to-analog current converters (DACs). The DACs also receives the above-noted reference current, which is amplified by the DACs in fine increments by appropriate selection of fine current control signals. When the coarse and fine current control circuitry are used in tandem, ample current with a fine current resolution can be achieved at any electrode and in a space- and power-efficient manner.

25 Claims, 14 Drawing Sheets

CURRENT GENERATION ARCHITECTURE FOR AN IMPLANTABLE STIMULATOR DEVICE HAVING COARSE AND FINE CURRENT CONTROL

CROSS-REFERENCE TO RELATED APPLICATIONS

This application is a continuation of U.S. patent application Ser. No. 11/550,763, filed Oct. 18, 2006, which in turn is a continuation-in-part of U.S. patent application Ser. No. 11/177,503, filed Jul. 8, 2005. Priority is claimed to both of these applications, and both are incorporated herein by reference.

FIELD OF THE INVENTION

The present invention relates generally to implantable stimulator devices, e.g., a pulse generator used for example in a Spinal Cord Stimulation (SCS) system. More particularly, the present invention relates to the current source/sink architecture used to supply currents to/from the electrodes of the device.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The present invention may find applicability in all such applications, although the description that follows will generally focus on the use of the invention within a Spinal Cord Stimulation (SCS) system, such as that disclosed in U.S. Pat. No. 6,516,227 ("the '227 patent"), issued Feb. 4, 2003 in the name of Paul Meadows et al., which is incorporated herein by reference in its entirety.

Spinal cord stimulation is a well-accepted clinical method for reducing pain in certain populations of patients. As shown in FIG. 1, a SCS system typically includes an Implantable Pulse Generator (IPG) 100, which includes a biocompatible case 116 formed of titanium for example. The case 116 holds the circuitry and power source or battery necessary for the IPG to function. The IPG 100 is coupled to electrodes 106 via one or more electrode leads (two such leads 102 and 104 are shown), such that the electrodes 106 form an electrode array 110. The electrodes 106 are carried on a flexible body 108, which also houses the individual signal wires 112, 114 coupled to each electrode. The signal wires 112, 114 are in turn connected to the IPG 100 by way of an interface 115, which allows the leads 102 and 104 to be removably connected to the IPG 110. Exemplary connector arrangements are disclosed in U.S. Pat. Nos. 6,609,029 and 6,741,892, which are incorporated herein by reference. In the illustrated embodiment, there are eight electrodes on lead 102, labeled $E_1$-$E_8$, and eight electrodes on lead 104, labeled $E_9$-$E_{16}$, although the number of leads and electrodes is application specific and therefore can vary.

The electrode array 110 is typically implanted along the dura of the spinal cord, and the IPG 100 generates electrical pulses that are delivered through the electrodes 106 to the nerve fibers within the spinal column.

Further details concerning the structure and function of typical IPGs, as well as IPG systems including telemetry and powering/recharging details, are disclosed in many of the documents incorporated by reference into this disclosure, with which the reader is assumed familiar.

An IPG 100 may include current source/sink circuitry that is configured to supply/receive stimulating current to/from the electrodes 106 on the IPG, and ultimately to/from tissue. For example, FIG. 2 shows an exemplary current source 500 and a corresponding current sink 501 used to stimulate tissue, exemplified generically as a load 505 (R). As one skilled in the art will understand, transistors M1 and M3 in the current source 500, and transistors M2 and M4 in the current sink 501, comprise a current mirror. However, other current source or sink circuitry can be used, such as that disclosed in U.S. patent application Ser. No. 11/138,632 ("the '632 application"), filed May 26, 2005, which is incorporated herein by reference in its entirety.

Both the source 500 and sink 501 are coupled to a current generator 506 configured to generate a reference current, $I_{ref}$. A suitable reference current generator is disclosed in U.S. Pat. No. 6,181,969 ("the '969 patent"), issued Jan. 30, 2001 in the name of inventor John C. Gord, which is incorporated herein by reference in its entirety. The reference current in both the current source/sink 500/501 is input into a digital-to-analog converter (DAC) configured to regulate the current that is sourced to or sunk from the load 505. Thus, source circuitry 500 employs DAC circuitry 502, while sink circuitry 501 employs DAC circuitry 503.

DAC circuitry 502, 503 is configured to regulate and/or amplify $I_{ref}$ and to output an output current $I_{out}$. Specifically, the relation between $I_{out}$ and $I_{ref}$ is determined in accordance with input control bits arriving on busses 513, 513', which gives DAC circuitry 502, 503 its digital-to-analog functionality. Essentially, in accordance with the values of the various M control bits on bus 513, any number of output stages (i.e., transistors M1, M2) are tied together in parallel such that $I_{out}$ can range from $I_{ref}$ to $2^M * I_{ref}$ in increments of $I_{ref}$, as will be explained in further detail later with reference to FIG. 4.

As shown in FIG. 2 for simplicity, current source circuitry 500 is coupled to an electrode $E_X$ on the IPG device 100, while current sink circuitry 501 is coupled to a different electrode $E_Y$ on the IPG device. However, in accordance with the approach disclosed in the '969 patent, each electrode on the device is actually hard-wired to both an current source 500 and an current sink 501, only one (or neither) of which is activated at a particular time to allow the electrode to selectively be used as either a source or sink (or as neither). This is shown in FIG. 3, which shows four exemplary electrodes $E_1$, $E_2$, $E_3$, and $E_4$, each having their own dedicated and hard-wired current source 500 and sink 501 circuitry. A primary clinical benefit of having the ability control current on each electrode is that it allows precise shaping of the electric field used for stimulation from the array of electrodes. Systems without this ability have less control of the field and are subject to variations and changes in impedance among electrodes.

The current source 500 and sink 501 circuitry hard-wired at each electrode are sometimes respectively referred to as PDACs and NDACs, reflecting the fact that the sources 500 are typically formed of P-type transistors while the sinks 501 are typically formed of N-type transistors. The use of transistors of these polarities is sensible given that the source is biased to a high voltage (V+), where P-type transistors are most logical, while the sink is biased to a low voltage (V−), where N-type transistors are most logical, as shown in FIG. 2. The substrate connection (not shown) for the transistors would typically be tied to the appropriate power supply, either V+ or V−, but could also be tied to the transistors' sources.

As shown in FIG. 3, the current sources (PDACs) and sinks (NDACs) active at any given time can be programmed. Thus, as shown, the source circuitry at electrode $E_2$ on the IPG is currently active, while the sink circuitry at electrode $E_3$ is also currently active. At a later time, electrodes $E_2$ and $E_3$ could be switched such that $E_2$ now operates as the sink, while $E_3$ operates as the source, or new sources or sinks could be chosen, etc., depending on how the logic in the IPG is programmed in accordance with optimal therapy for the patient in which the IPG is implanted.

A consequence of this architecture is that, as mentioned, each electrode has its own dedicated source (i.e., PDAC) and sink (i.e., NDAC) circuitry. Further details of such dedicated current source circuitry 500 for a particular electrode (e.g., $E_X$) as disclosed in the '969 patent is shown in FIG. 4. Dedicated current sink circuitry 501 for each electrode, similar to the current source circuitry 500 but differing in polarity (see e.g., FIG. 2), would likewise be hardwired to the electrode $E_X$, but is not shown for convenience in FIG. 4. (However, both the source and sink circuitry are shown in a simplified manner in FIG. 7). Also not shown for convenience is the presence of a coupling capacitor typically hardwired at each electrode Ex (see '969 patent, FIG. 3, element 203).

The source circuitry of FIG. 4 can be programmed to output a source current of a particular magnitude. Specifically, the circuitry as shown is capable of outputting to the electrode Ex a current $I_{out}$ ranging from $I_{ref}$ to $127I_{ref}$ in increments of $I_{ref}$, depending on the status of the control bits (Bit<1:M>). This occurs as follows: each control bit, when selected, contributes $2^{(M-1)}$ worth of current to the output current, $I_{out}$, through activation of pass transistors 530 in each of the M stages that comprise the current source. For example, if a current of $53I_{ref}$ is desired at $I_{out}$, control bits Bit<1, 3, 5, 6> would be enabled (active low) to turn on transistors $530_1$, $530_3$, $530_5$, and $530_6$, which respectively contribute $I_{ref}$, $4I_{ref}$, $16I_{ref}$ and $32I_{ref}$, in sum, $53I_{ref}$. Although each stage is shown as having its own current source $I_{ref}$ it would usually be the case that each stage taps into a singular reference current (not shown for convenience), which is preferred to ensure current uniformity across the stages.

However, this current source/sink architecture of FIGS. 3 and 4 does not comprise an efficient use of space on the integrated circuit in the IPG on which the current source/sink circuitry is fabricated. In a typical SCS system implementation, the IPG might contain 16 electrodes, $E_1$ through $E_{16}$. However, it is usually the case that only one PDAC (source) and one NDAC (sink) are active at one time. Or, more rarely, four or more PDACs (sources) or NDACs (sinks) might be active at one time. Even in such an extreme case, it will be noted that the majority of the PDACs (source) and NDACs (sinks) are inactive. Furthermore, even for those electrodes that are active at a particular time, only one of the source 500 or sink 501 circuitry for that electrode can be active. The result is that, most of the time, most of the PDACs or NDACs in the IPG 100 are not being utilized. When one considers that the PDACs or NDACs take up significant space on the integrated circuit (see FIG. 4), the provision of such redundancy for every electrode seems inefficient.

Another current source/sink architecture is disclosed in the above-incorporated '227 patent, and in particular in FIG. 4A of the '227 patent, salient aspects of which are summarized in the present application in FIGS. 5 and 6. As shown in FIG. 5, the architecture of the '227 patent also uses a plurality of current sources and sinks, and further uses a low impedance switching matrix that intervenes between the sources/sinks and the electrodes $E_X$. Notice that each source/sink pair is hard-wired together at nodes 333, such that the switching matrix intervenes between the common nodes 333 and the electrodes. Of course, only one of the source or the sink in each pair is activated at one time, and thus point 333 in any pair will source or sink current at any particular time. Through appropriate control of the switching matrix, any of the nodes 333 (and hence any of the PDAC/NDAC pairs) may be connected to any of the electrodes $E_X$ at any time.

While generally a suitable architecture, the architecture of FIGS. 5 and 6 suffer from drawbacks. For one, this architecture puts additional resistance—namely the resistance of the switches in the switching matrix—in the output path between the power supply in the DAC circuitry and the electrode. As explained in the above-incorporated '632 application, it is generally desired to minimize resistance between the power supply and the electrode. Thus, and referring to FIG. 6, which shows the architecture of FIG. 5 in further detail, it is desired that the resistance be minimized in the output path between the power supply V+ or V− and a given electrode $E_X$. This is because any resistance in the output path will give rise to a voltage drop in the output path (the output path resistance times $I_{out}$) which is not otherwise useful in the context of the circuitry. But in the architecture of FIGS. 5 and 6, it can be seen that three elements are serially connected between the power supplies and the electrode: the current mirror, the bit select transistor, and the transistor (switch) in the low impedance switch matrix. Due to the additional resistances of these components, and specifically the additional resistance of the switches in the switch matrix, power (i.e., the output path resistance times $I_{out}^2$) is wasted. In an implantable stimulator device, such unnecessary power loss is regrettable, because battery life in such devices is critical and beneficially made as long as possible.

Moreover, the architecture of FIGS. 5 and 6 is further inefficient from a layout perspective. Due to the common node 333 between a given PDAC source and NDAC sink pair, only one DAC in each pair can be active at any time. Thus, and like the architecture of FIGS. 3 and 4, DAC circuitry is guaranteed to go unused at any particular time. More specifically, at least 50% of the DAC circuitry (the unselected DAC in a pair), and likely more, will go unused at any given time, which again is a wasteful use of layout on the integrated circuit.

In short, the implantable stimulator art, or more specifically the IPG or SCS system art, would be benefited by an architecture that allows variable currents to be provided at a number of electrodes, but in a more space-efficient manner.

Additionally, such an improved architecture would also preferably allow for fine adjustments to the current to be sourced or sunk. In this regard, it has been recognized in the art that it can be beneficial to finely adjust the amount of current sourced or sunk at a particular electrode in increments less than $I_{ref}$. For example, in the above-reference '969 patent, and as shown here in FIG. 7, it is disclosed that the source/sink circuitry 500/501 can include a stage or stages 550 which provide a fraction of the reference current, $I_{ref}$. These stages 550, are controlled by another control bit, Bit<0> (designated as "0+" for the source and "0−" for the sink). Specifically, it is noted in the '969 patent that fractional values of $(\frac{1}{2})^m$ (i.e., $\frac{1}{2}*I_{ref}$, $\frac{1}{4}*I_{ref}$, $\frac{1}{8}*I_{ref}$ etc.) or 1/m (e.g., $\frac{1}{2}*I_{ref}$, $\frac{1}{3}*I_{ref}$ etc.), or multiple values thereof, can be provided by stage or stages 550. See '969 patent, col. 6, 1. 43 to col. 7, 1. 6.

By providing the ability to include fractions of the reference current, $I_{ref}$, in the overall current, fine adjustments (via stages 550) can be made to the otherwise coarse current adjustments provided by the remainder of the circuitry. However, the overall result is still one which is not terribly space efficient, because, as noted above, much of the current source and sink circuitry is guaranteed to be unused at any given time.

SUMMARY

Disclosed herein is a current generation architecture for an implantable stimulator device such as an Implantable Pulse Generator (IPG) or more specifically for a Spinal Cord Stimulation (SCS) system. In the architecture, current source and sink circuitry are both divided into coarse and fine portions, which respectively have the ability to provide a coarse and a fine amount of current to a specified electrode on the IPG.

The coarse portion of the current generation circuitry is distributed across all of the electrodes and so can source or sink current to any of the electrodes. Specifically, the coarse portion is divided into a plurality of stages, each of which is capable via an associated switch bank of sourcing or sinking an amount of current to or from any one of the electrodes on the device. Each stage is preferably formed of a current mirror for receiving a reference current and outputting a current to that stage's switch bank. The output current in the stage preferably represents a scaled version of the reference current, i.e., the output current comprises the reference current times a scalar at the stage, which can be set by wiring a desired number of output transistors in the current mirror in parallel. In a preferred embodiment, the scalars of the different stages are uniformly set to provide a coarse increment of the reference current to the switch banks, and hence to any of the electrodes.

The fine portion of the current generation circuitry, in the preferred embodiment, includes source and sink circuitry dedicated to each of the electrode on the device. The dedicated circuitry preferably comprises digital-to-analog current converters (DACs). The DACs include a current mirror and also receive the above-noted reference current. The reference current is amplified in the DACs in fine increments by appropriate selection of fine current control signals. When the coarse and fine current control circuitry are used in tandem, sufficient current with fine current control can be achieved at any electrode and in a space- and power-efficient manner.

BRIEF DESCRIPTION OF THE DRAWINGS

The above and other aspects of the present invention will be more apparent from the following more particular description thereof, presented in conjunction with the following drawings wherein.

Corresponding reference characters indicate corresponding components throughout the several views of the drawings.

DETAILED DESCRIPTION

The following description is of the best mode presently contemplated for carrying out the invention. This description is not to be taken in a limiting sense, but is made merely for the purpose of describing the general principles of the invention. The scope of the invention should be determined with reference to the claims and their equivalents.

At the outset, it is noted that the present invention may be used with an implantable pulse generator (IPG), or similar electrical stimulator and/or electrical sensor, that may be used as a component of numerous different types of stimulation systems. The description that follows relates to use of the invention within a spinal cord stimulation (SCS) system. However, it is to be understood that the invention is not so limited. Rather, the invention may be used with any type of implantable electrical circuitry that could benefit from efficient current source/sink circuitry. For example, the present invention may be used as part of a pacemaker, a defibrillator, a cochlear stimulator, a retinal stimulator, a stimulator configured to produce coordinated limb movement, a cortical and deep brain stimulator, or in any other neural stimulator configured to treat urinary incontinence, sleep apnea, shoulder sublaxation, etc.

As noted earlier, exemplary embodiments of the present invention involve the architecture used in the current source and sink circuitry, which are sometimes respectively referred to as the PDAC and NDAC circuitry. Previous approaches were summarized in the Background section of this disclosure. But as noted, these architectures suffered from various drawbacks.

A new and improved current generation architecture is illustrated in FIGS. 8-13. The new architecture, like previous architectures, employs current source and current sink circuitry, respectively labeled in FIGS. 8A and 8B as circuitry 400 and 401, which would logically be implemented for example on analog IC. As shown, the source circuitry 400 is in solid lines while the sink circuitry 401 is illustrated in mere dotted lines. However, the sink circuitry 401, while not specifically discussed, is similar in design and function to the source circuitry 400, although differing in polarity (e.g., connection to negative power supply V−, use of N-channel transistors, etc.). In other words, for simplicity, and to avoid redundancy, the source circuitry 400 is specifically discussed in this disclosure, although it should be understood that the sink circuitry 401 is similar in all material respects and of equal importance.

Figure 8A:
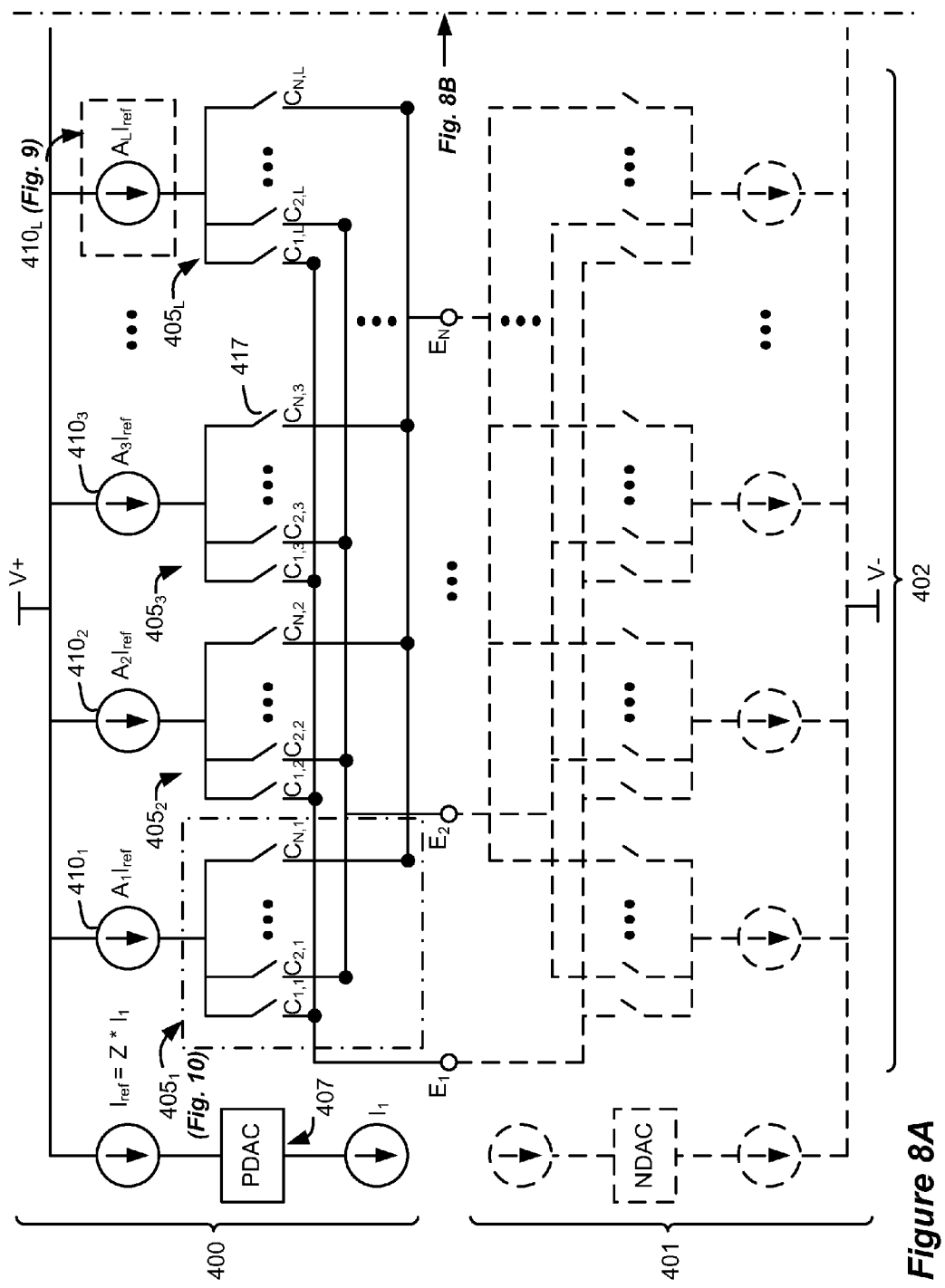
FIGS. 8A and 8B illustrates an improved current source/sink architecture having both coarse and fine current control in accordance with one embodiment of the invention.
Figure 8B:
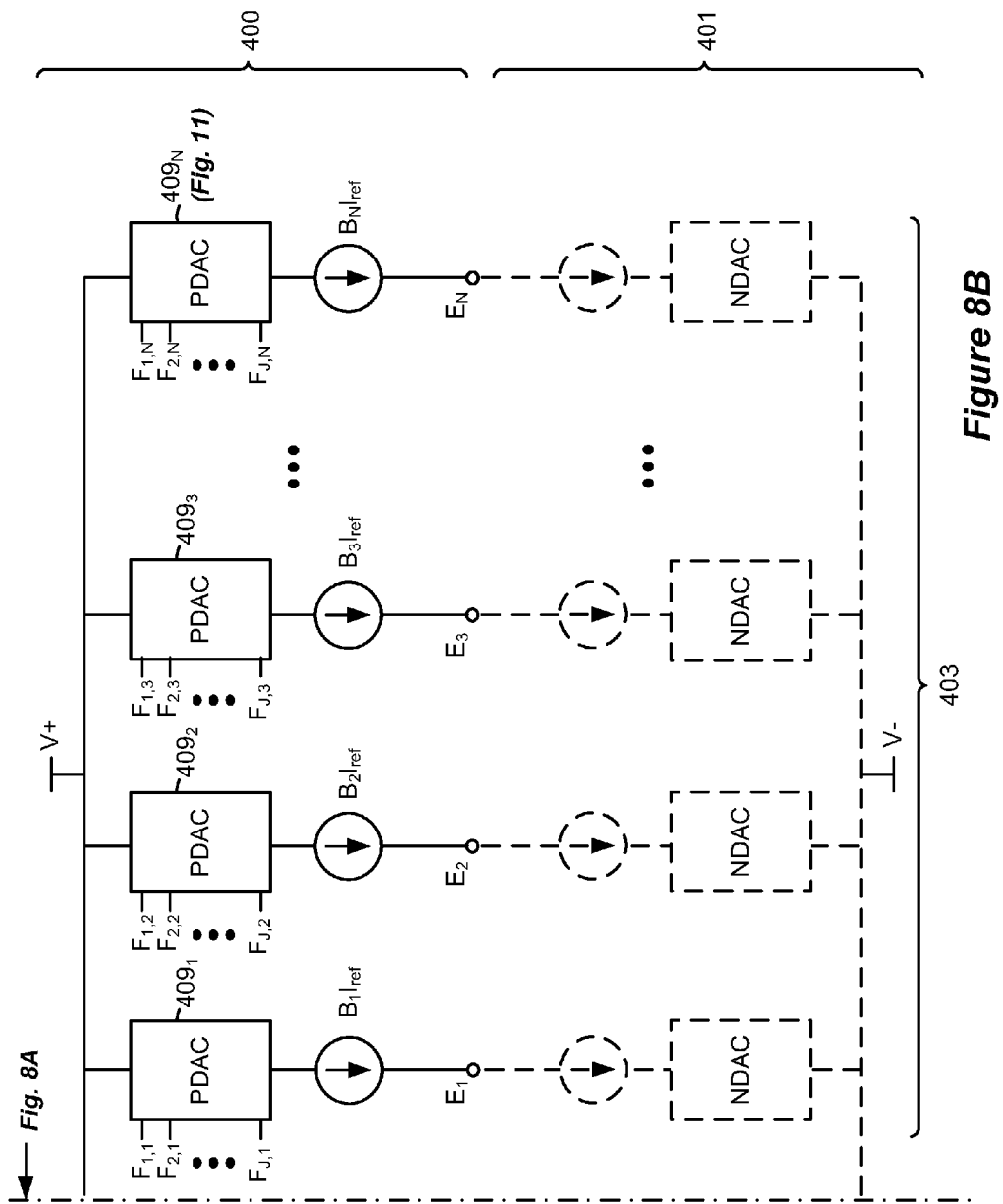

As is unique to the new architecture, each of the source/sink circuitry 400/401 is divided into two parts: a coarse portion 402 (FIG. 8A) and a fine portion 403 (FIG. 8B). As its name suggests, the coarse portion 402 allows a coarse amount of current to be provided to a particular electrode. In other words, the amount of current which can be programmed to be source or sunk at a particular electrode by the coarse portion 402 is incrementable in relatively-large increments. By contrast, the amount of current which can be programmed to be sourced or sunk at a particular electrode by the fine portion 403 is incrementable in relatively-small increments. Having both coarse and fine portions 402 and 403 allows for efficient and dynamic control of the current at a particular electrode, as will be explained further below.

Because they are different in their architecture and operation, the coarse and fine portions 402/403 of the current circuitry are separately discussed, with the coarse portion 402 discuss first.

Figure 1:
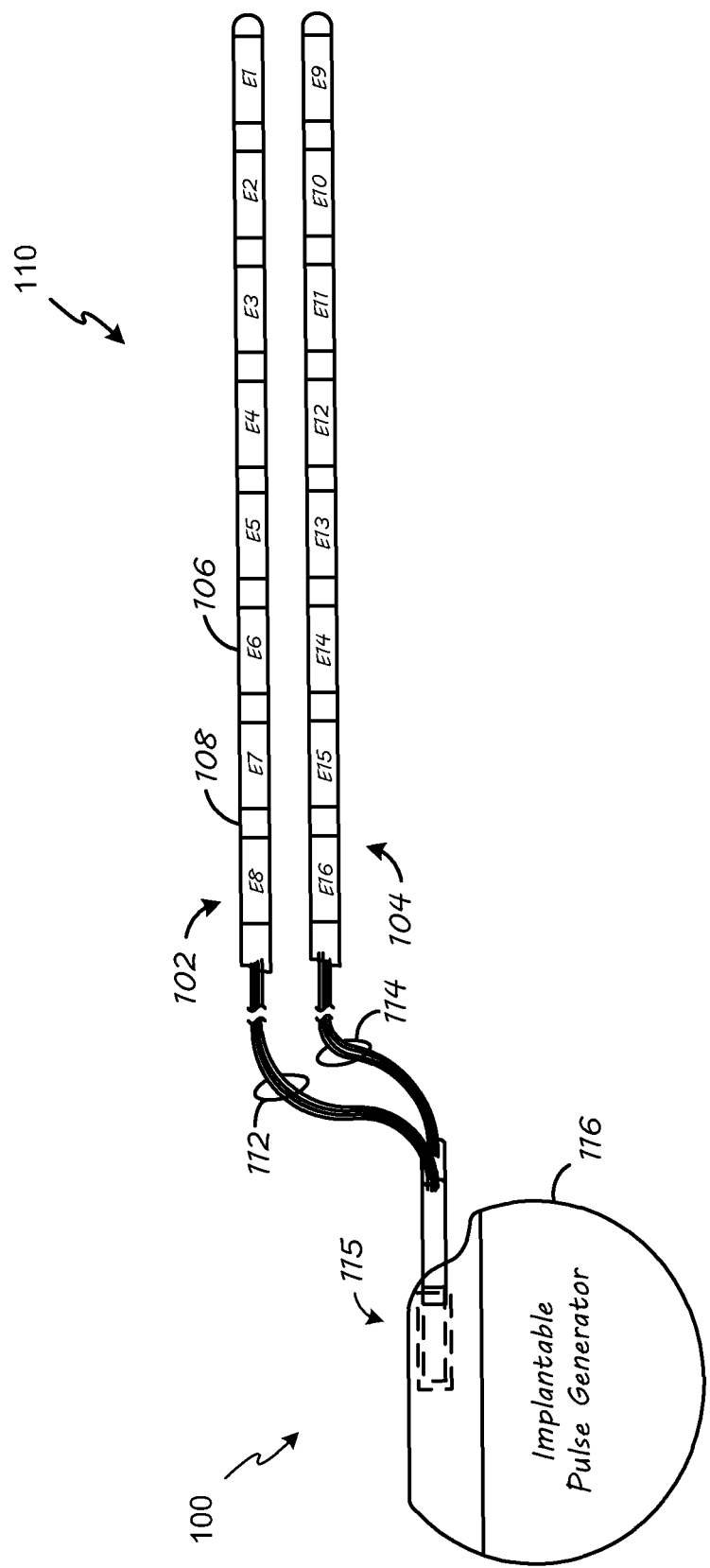
FIG. 1 shows an exemplary implantable pulse generator (IPG) and its associated electrode array in accordance with the prior art.
Figure 2:
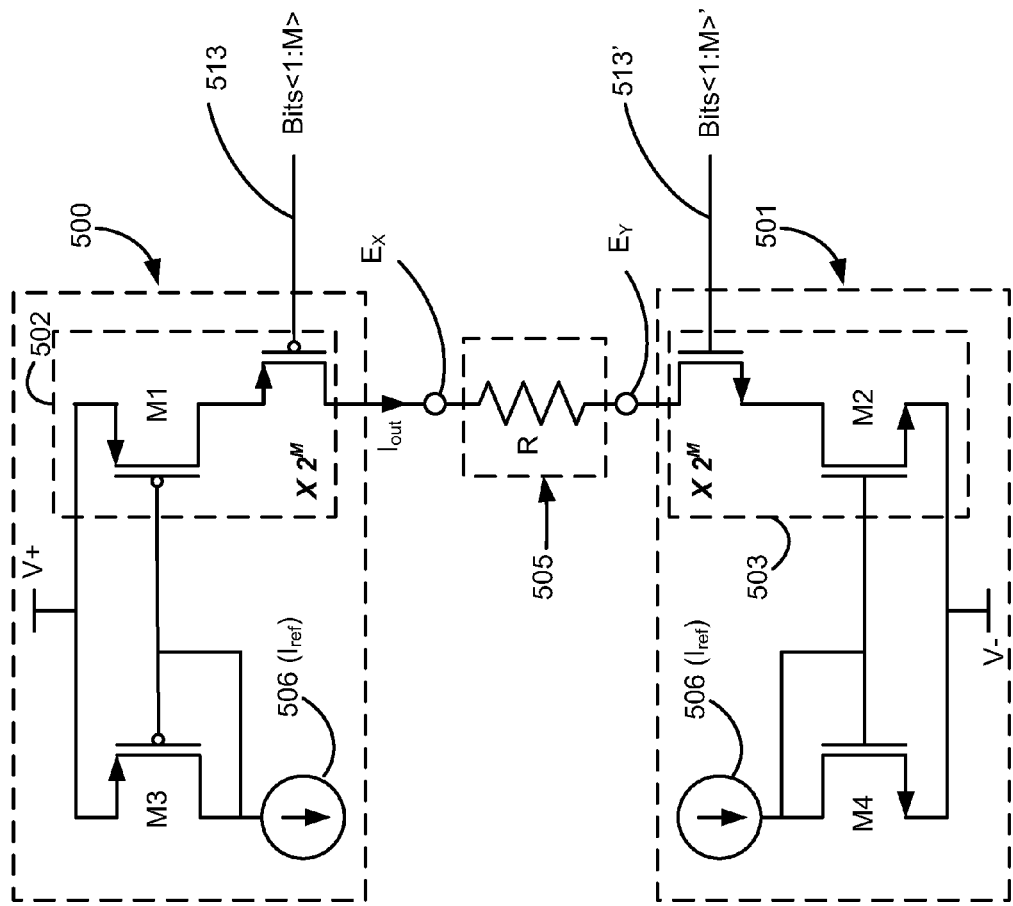
FIG. 2 shows an exemplary prior art current source and a corresponding current sink for an IPG, each having current digital-to-analog converter (DAC) circuitry in series with a load.
Figure 3:
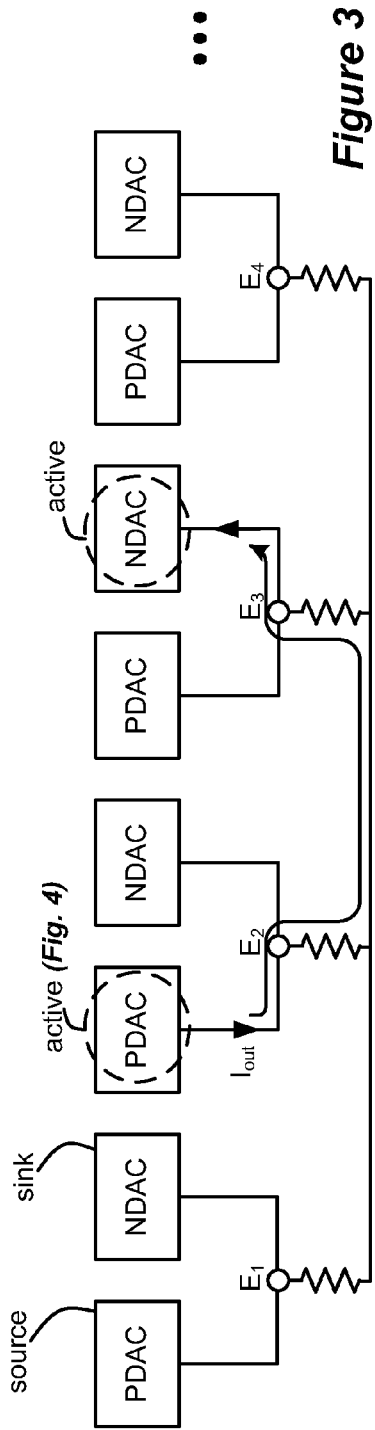
FIG. 3 shows a prior art architecture for coupling current sources and sinks to a plurality of electrodes using hard-wired dedicated circuitry at each electrode.
Figure 4:
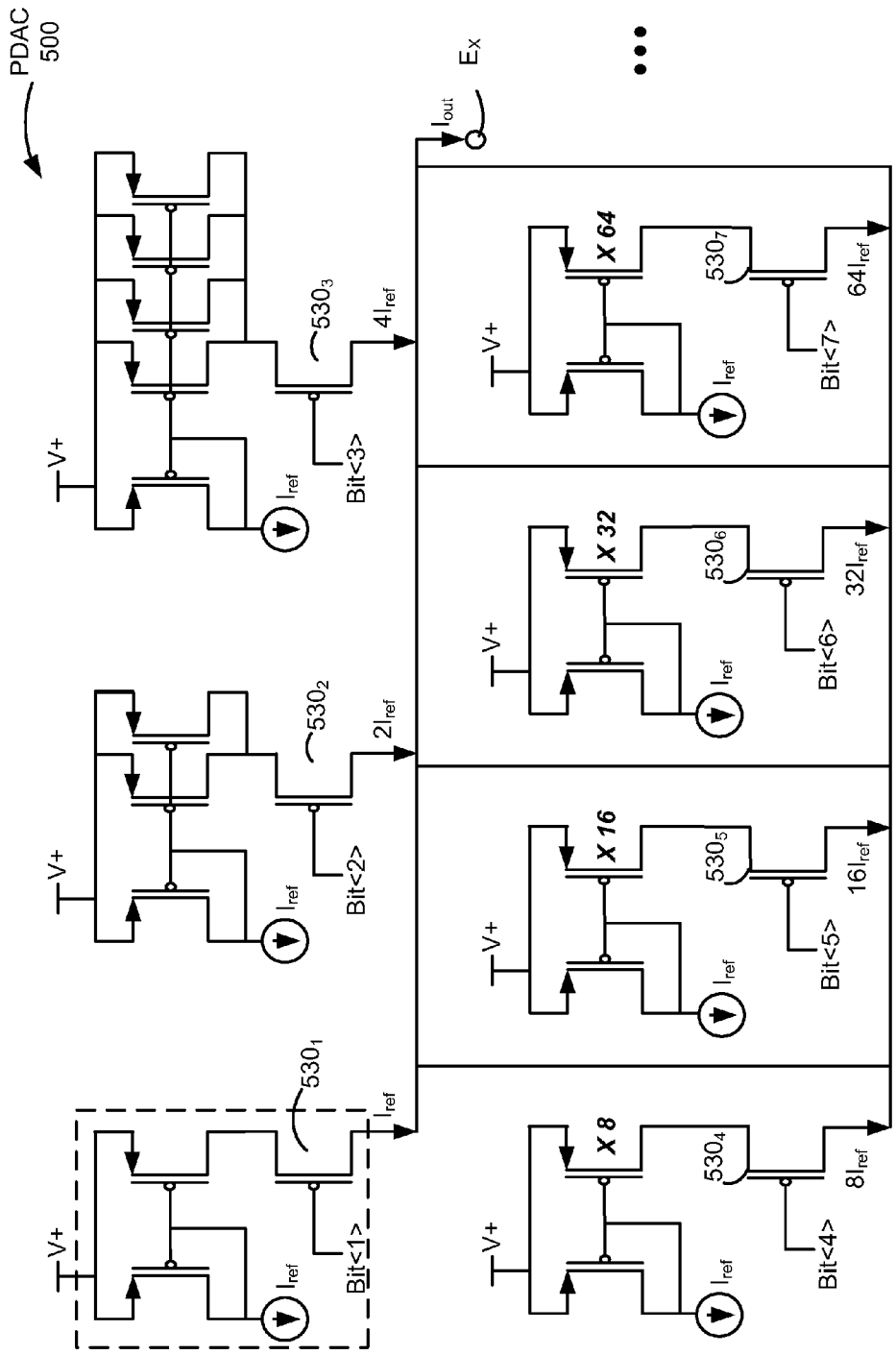
FIG. 4 shows the layout complexity of one of the current sources of FIG. 3.

Unlike the prior art architecture of FIGS. 3 and 4, the coarse current circuitry 402 preferably does not involve dedicating or hard-wiring source and sink circuitry to each electrode $E_1$ through $E_N$ on the IPG 100. Instead, the coarse portion 402 of the source and sink circuitry 400, 401 is shared or distributed amongst the various electrodes via a network of switch banks 405, as will be explained below.

Figure 10:
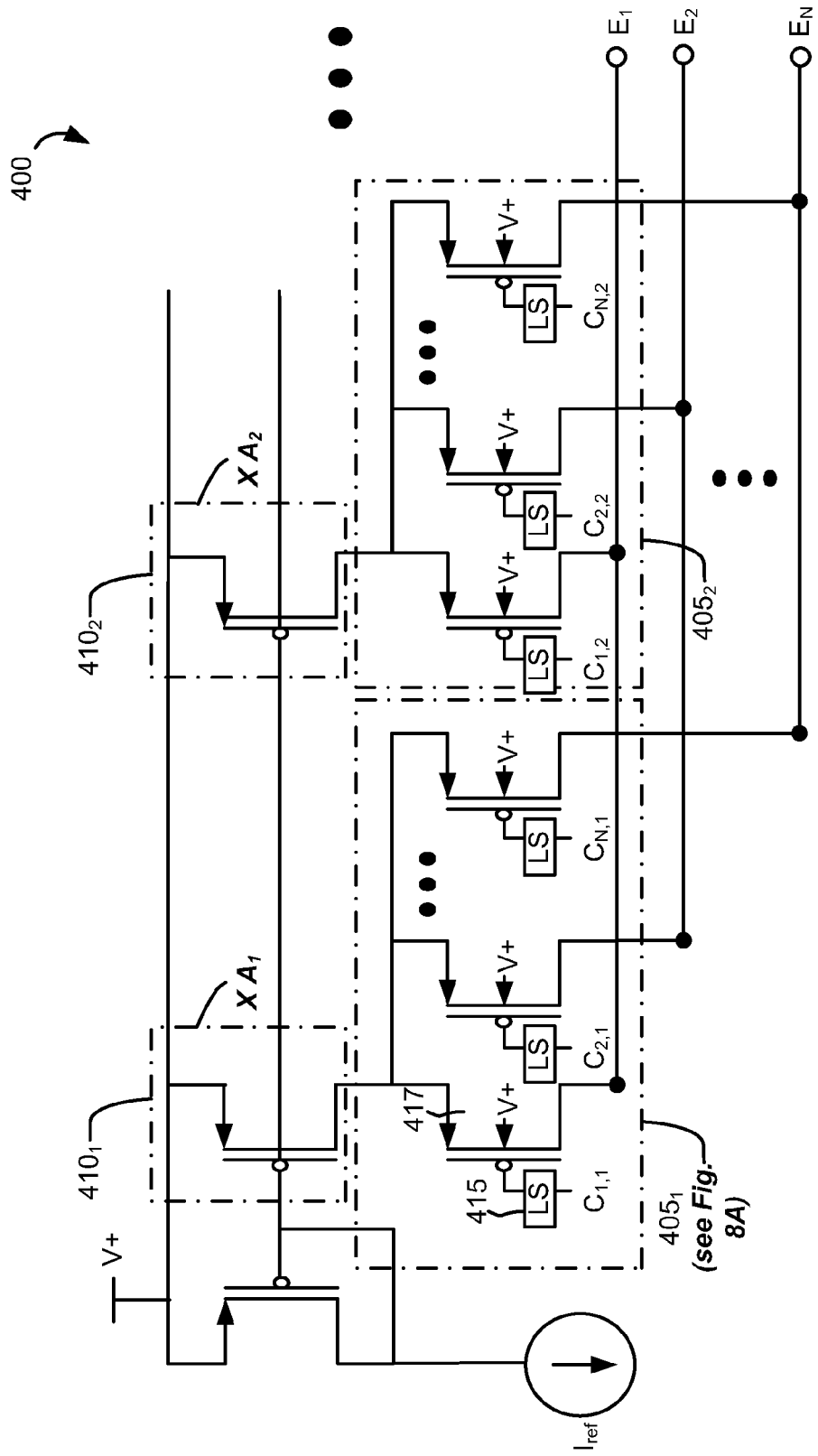
FIG. 10 shows the switch banks used in the coarse circuitry portion to distribute a coarse amount of current from any of the current mirrors to any of the electrodes.

As shown, the source circuitry 400 comprises various current mirrors 410 and various switch banks 405. Specifically, there are L number of current mirrors 410 and switch banks 405. Each switch bank comprises N switches, which corresponds to the number of electrodes on the IPG 100. Thus, there are a total of N*L switches 417 in the switch banks 405, controlled by N*L control signals ($C_{N,L}$). As shown in FIG. 10, the control signals to the switches 417 may need to be level shifted to DC values appropriate for the switches 417, which can easily occur via level shifters 415, as one skilled in the art will understand. The switches 417 are preferably single transistors of a logical polarity depending on whether they are present in the source circuitry 400 (P-channels) or the sink circuitry 401 (N-channels). However, other structures could also be used for the switches 417, such as pass gates or transmission gates, etc.

The current mirrors 410 in the coarse portion 402 receive a reference current, $I_{ref}$. Because it may be useful to set this reference current to a particular value, a PDAC 407 can be used to convert an initial reference current $I_1$ to the true reference current $I_{ref}$ sent to each of the current mirrors 410. The PDAC 407 can comprise any structure known in the art for programming the amplification of a current on the basis of digital inputs. For example, the PDAC can be constructed as in FIG. 4. As shown, the PDAC 407 scales the initial reference current $I_1$ by a factor of Z to produce the true reference current $I_{ref}$. In this way, the currents ultimately sent to the electrodes can be further (and globally) varied by adjusting the gain of the PDAC 407. If smaller current resolutions are required in both the coarse and fine portions 402 and 403, Z can be reduced through appropriate digital control of the PDAC. If higher total currents are required, Z can likewise be increased. Additionally, because PDAC 407 is digitally controllable, it can be controlled to different values at different points in time. This being said however, PDAC 407 is not required in all embodiments of the invention, and the reference current $I_{ref}$ can be provided in different ways.

The various current mirrors 410 take the reference current $I_{ref}$ and scale that current to produce currents of desired magnitudes in each of the L stages of the coarse portion 402. Thus, the first stage scales $I_{ref}$ by $A_1$, the second by $A_2$, and so on. The various scalars $A_1, A_2, \ldots A_L$, can be different or can be the same in each of the stages. For example the scalars can exponentially increase ($A_1=1$, $A_2=2$, $A_3=4$, $A_4=8$, etc.), or linearly increase ($A_1=1$, $A_2=2$, $A_3=3$, etc.), or can stay the same. (In this sense, a current can be said to be "scaled" even if the scalar at the stage equals one).

Figure 9:
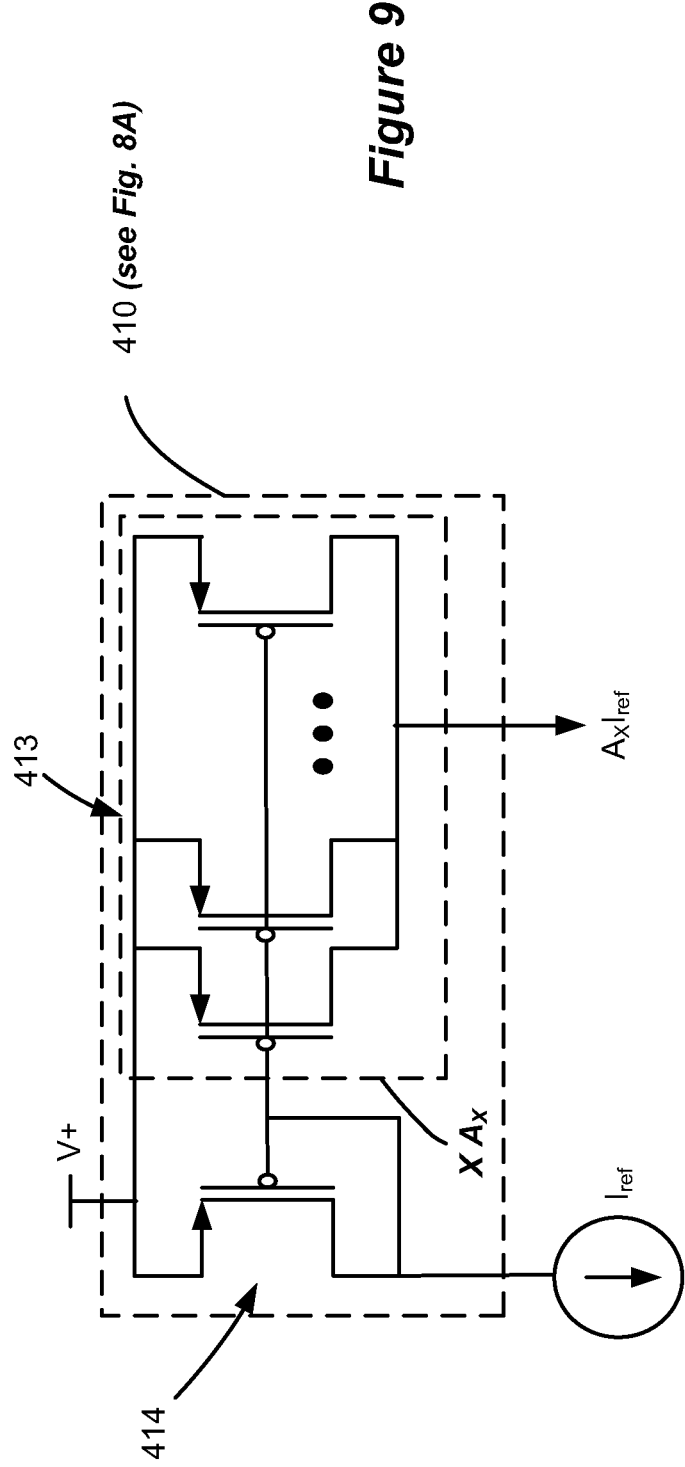
FIG. 9 shows the current mirror circuitry useable in the coarse circuitry portion of the architecture of FIGS. 8A and 8B.

In an exemplary embodiment, each of the scalars $A_1$ to $A_L$ are set to the same value of 5 and thus each of the L stages outputs the same amount of current ($5I_{ref}$) to their respective switch banks 405. To set this amount of gain at each of the L stages, five transistors 413 are placed in parallel with the balancing transistor 414 in the output stages of the current mirrors 410, as is shown in FIG. 9. However, it should be noted that current mirrors 410 are simply one example of a current converter, i.e., a circuit used to convert one current ($I_{ref}$) to another current ($A_x I_{ref}$). Many other circuits capable of performing this function are known in the art, as thus the use of current mirrors in each stage should be understood as merely exemplary.

In further distinction to the architecture of FIGS. 3 and 4, note that the current mirrors 410 in the coarse current circuitry 402 are not individually selectable in and of themselves, i.e., they do not have bit select transistors as in the DACs of FIGS. 3 and 4. They are always on and supplying current to the switch banks 405, with selection or not of a particular current mirror 410's current occurring in its given switch bank 405.

As shown in FIGS. 8A and 10, and as noted previously, each of the L switch banks 405 contains N switches, $S_N$, each of which is capable of routing the output current from its current mirror $410_x$ ($A_x I_{ref}$) to any of the electrodes $E_X$ on the IPG 100, depending on the status of the coarse current control signals $C_{N,L}$. Thus, in each stage X, control signal $C_{Y,X}$ can send that stage's current to $E_Y$. In other words, each stage is controllable to send its output current to more than one of the electrodes and thus can affect the current at any given electrode, and multiple stages can work together to produce a current at a given electrode.

For example, assume each current mirror 410 has a scalar A=5, such that each sends $5I_{ref}$ to its respective switch bank 405. Assume further that there are 19 stages, such that all current mirrors 410 together can supply a maximum current of $95I_{ref}$. If a current of $50I_{ref}$ was desired at electrode $E_2$, switches 417 could be closed in any 10 of the stages: the first 10 stages ($C_{2,1}$ to $C_{2,10}$); the last 10 stages, ($C_{2,10}$ to $C_{2,19}$); etc. Similarly, multiple electrodes can be stimulated at the same time. For example, suppose $50I_{ref}$ is desired at electrode $E_2$; $10I_{ref}$ at electrode $E_5$, and $15I_{ref}$ at electrode $E_8$. This could be achieved by simultaneously activating the following coarse control signals: ($C_{2,1}$ to $C_{2,10}$), ($C_{5,11}$ to $C_{5,12}$), ($C_{8,13}$ to $C_{8,15}$). Of course, at some point the total amount of current that can be sourced from the source circuitry 400 (or sunk to the sink circuitry 401) at any given time will be dictated by the load that the compliance voltage V+ can handle.

Not every stage L would necessarily require N switches. For example, a given stage might comprise less than N switches, foregoing the ability to send that stage's current to a particular electrode $E_X$. Moreover, it is not necessary that every Xth switch in the switch banks 405 provide current to the Xth electrode, $E_X$. In short, while FIG. 8A illustrates a preferred embodiment, other designs are possible that still achieve the benefits of the architecture disclosed herein.

Because the gain in each of the current mirrors 410 in the exemplary embodiment is A=5, the minimum current resolution provided by any one of the L current mirrors 410 is $5I_{ref}$, which can be considered as a coarse current resolution of the coarse portion 402 of the current source circuitry 400. Accordingly, to additionally provide the ability to make fine adjustments to the current provided at the electrodes, fine current source and sink circuitry 403 is also provided.

As shown in FIG. 8B, and unlike the coarse portion 402, fine portion 403 is preferably hard-wired to each of the N electrodes. In this respect, the fine portion 403 is similar to architecture of FIGS. 3 and 4, which likewise used dedicated source and sink circuitry at each electrode. As noted in the discussion of the architecture of FIGS. 3 and 4, the use of dedicated source and sink circuitry at each electrode can be inefficient (guaranteed unused circuitry, etc.). However, any inefficiency in this regard is offset by the concurrent use of the coarse circuitry 402 to set the current at any given electrode, as will be explained below.

In a preferred embodiment, and as shown in FIG. 8B, the fine portion 403 of the source circuitry 400 comprises a PDAC 409 at each electrode. (Additionally, each electrode will also preferably have a corresponding NDAC for sinking current, as shown in dotted lines in FIG. 8B, but not discussed for simplicity). Such PDACs 409 may be similar in design and architecture to the PDAC 407 used to set the reference current, $I_{ref}$ (see FIG. 8A), but again any current generation circuitry can be used.

Figure 11:
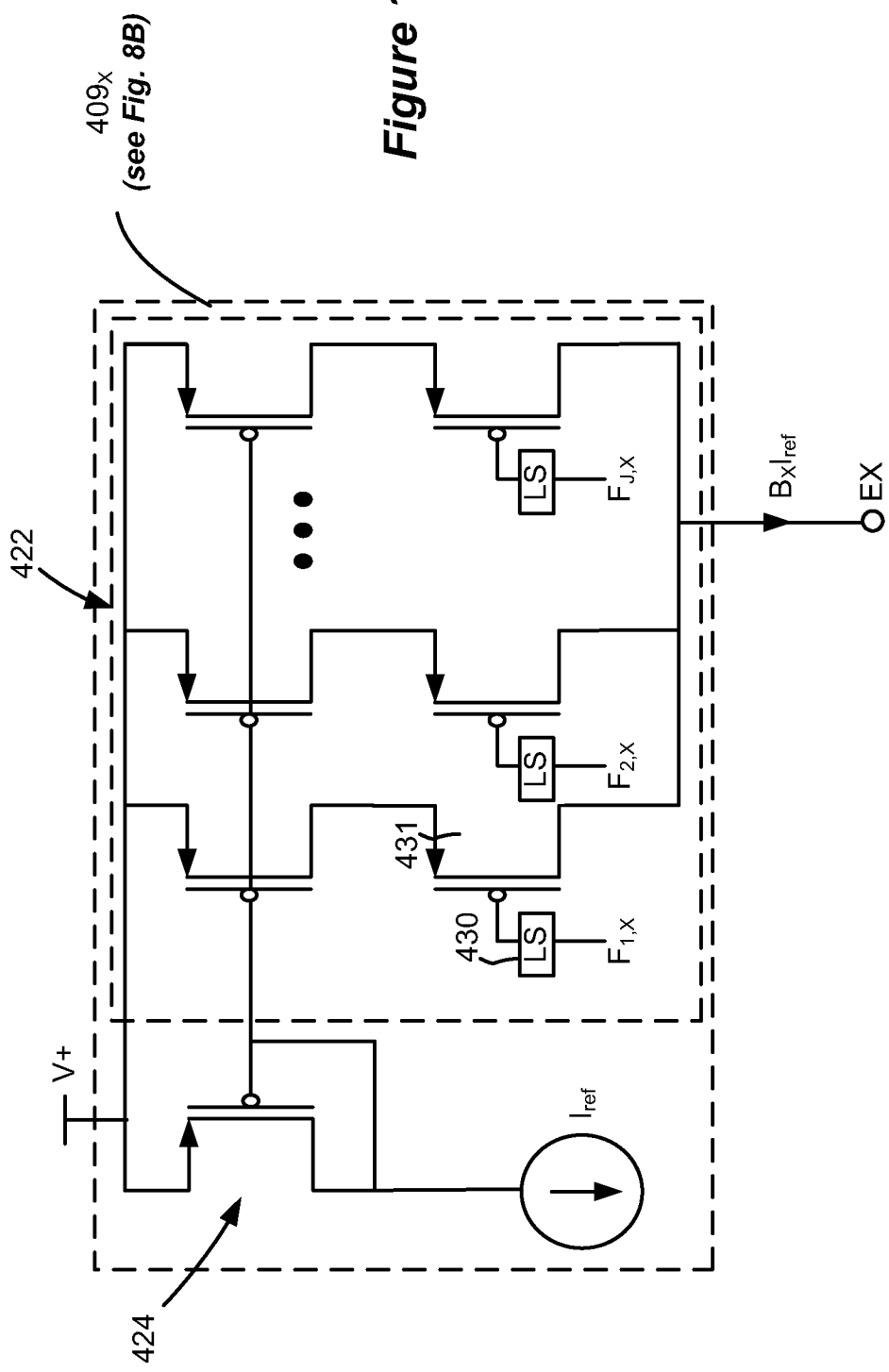
FIG. 11 shows the PDAC used in the fine circuitry portion of the architecture of FIGS. 8A and 8B which is dedicated at each electrode.
Figure 12A:
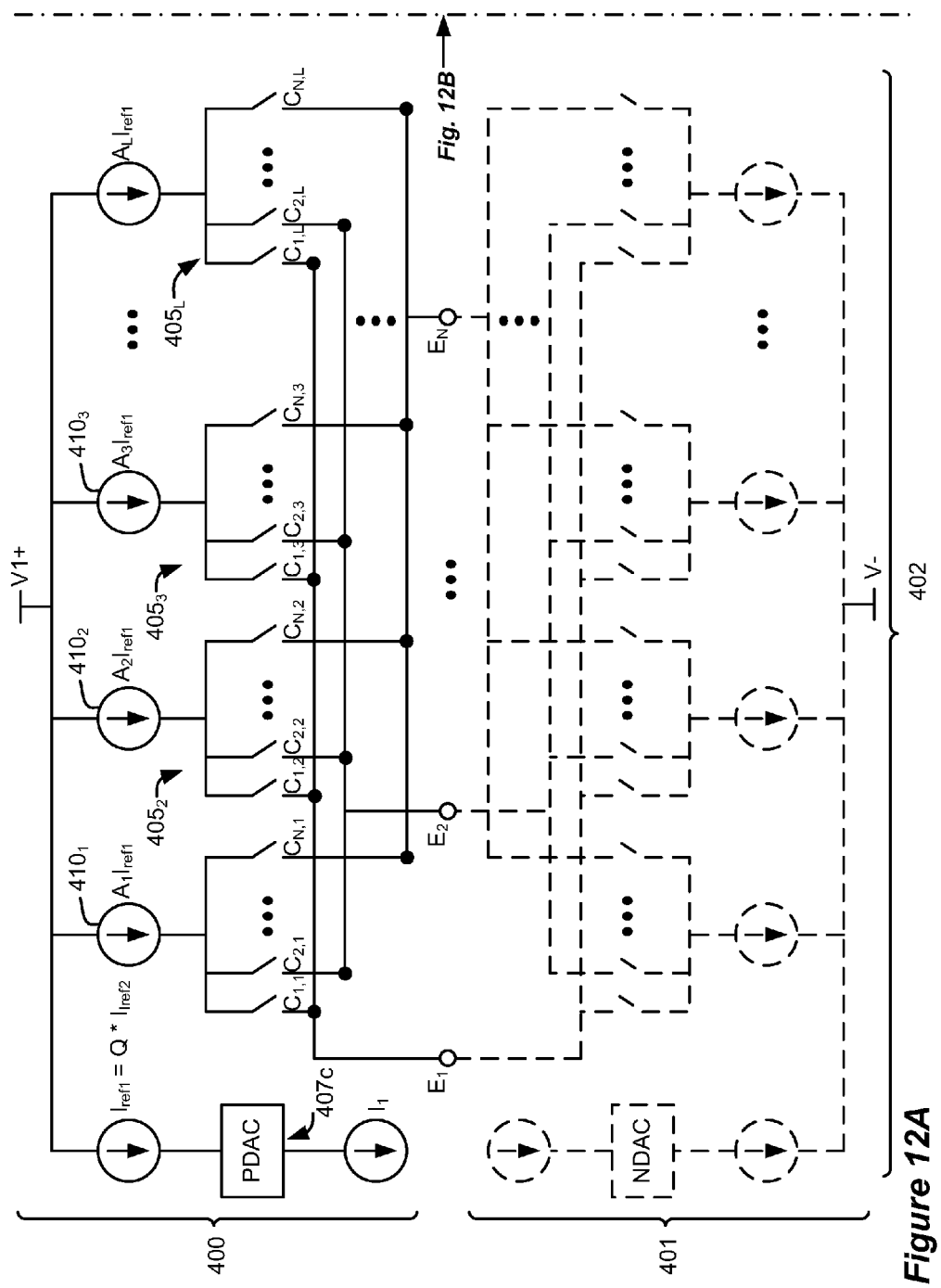
FIGS. 12A and 12B illustrate an alternative embodiment to that shown in FIGS. 8A and 8B in which two different reference currents are used for the coarse and fine portions.
Figure 12B:
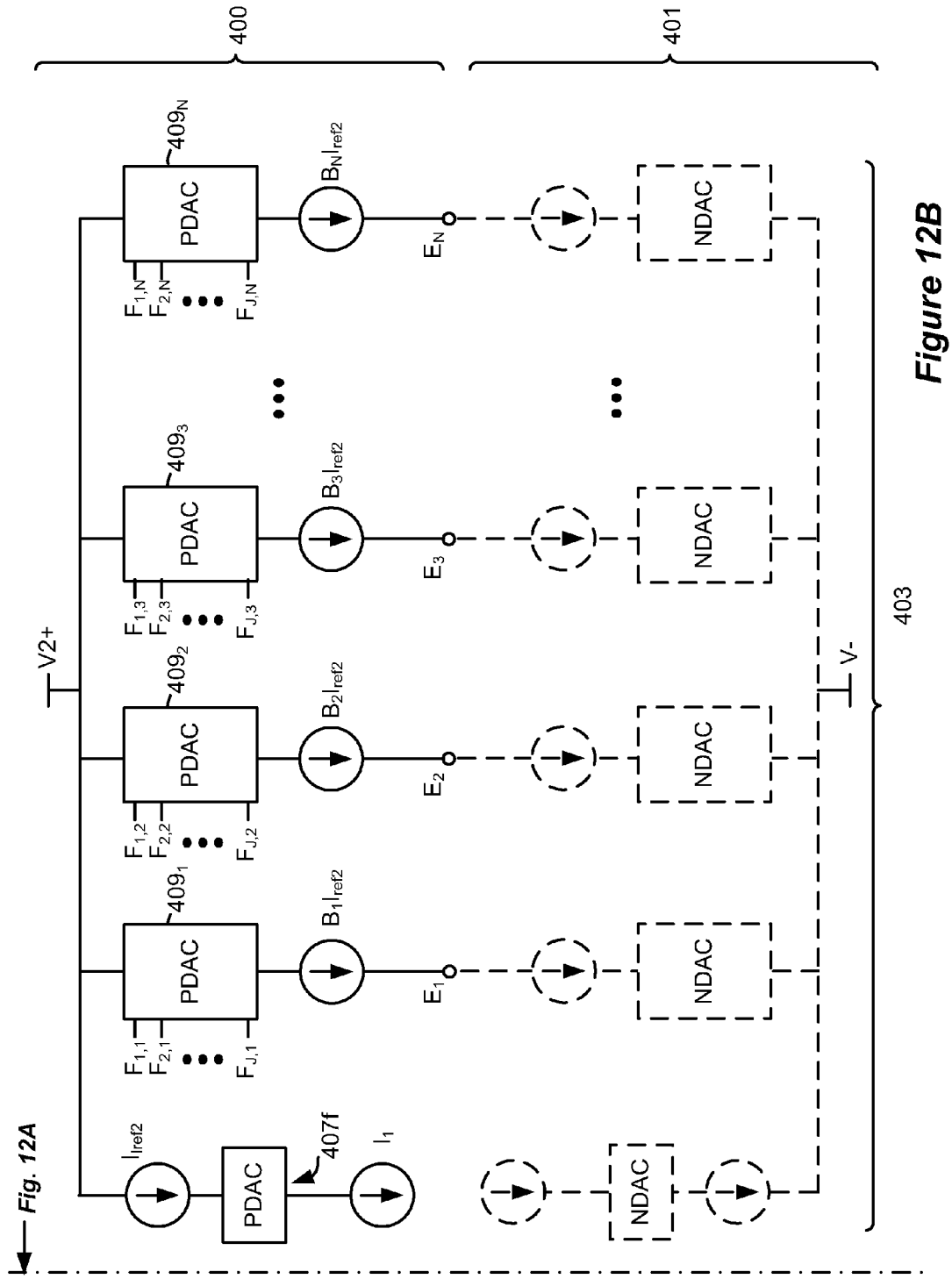

A preferred embodiment for the PDACs 409 used in the fine portion 403 of the source circuitry 400 is shown in FIG. 11. As can be seen both in FIGS. 8B and 11, each PDAC 409 receives the reference current from PDAC 407, $I_{ref}$ (see FIG. 8A), as well as fine current control signals ($F_{J,N}$) used to set the amount of current output by each PDAC 409. As FIG. 11 shows, each PDAC 409 preferably constitutes a current mirror having a balancing transistor 424 and a plurality (J) of output transistors 422 (stages), each gated by one of J control signals ($F_{1,X}$ to $F_{J,X}$). Each of the output transistors 422 are connected in parallel, and are allowed to contribute $I_{ref}$ (i.e., the input current) to the output current, depending on which of the selection transistors 431 are selected by fine current control signals $F_{J,N}$.

Because they are wired in parallel, the more fine current control signals enabled for any given stage, the higher the current output for that stage, which in effect sets the gain B for that stage. For example, if only $F_{1,X}$ is enabled for a given stage, then the current output from that stage equals $I_{ref}$ (i.e., B=1). If $F_{1,X}$ and $F_{2,X}$ are enabled, then the current output for stage (electrode) X equals $2I_{ref}$ (i.e., B=2), etc. In a preferred embodiment, J=4, such that there are four output transistors 431 in each stage, and therefore each stage (PDAC) 409 can output a maximum current of $4I_{ref}$, which of course requires that all fine current control signals (i.e., $F_{1,X}$ thought $F_{J,X}$) for a given stage (electrode) be activated. If necessary, level shifters 430 can be used to convert the fine control signals to appropriate levels to control the switches 431.

In other words, depending on the status of the control signals $F_{J,N}$ for each electrode, a minimum of $0I_{ref}$ and a maximum of $4I_{ref}$ in increments of $I_{ref}$ can be sourced by the fine portion 403 of the current source circuitry 400 for any given electrode $E_X$. (Again, the sink circuitry 401 would be similar). Note therefore that the fine portion 403 have a current resolution, $I_{ref}$, which is smaller than the current resolution of the coarse portion 402, $5I_{ref}$. Because of this different in resolution, both portions can be used simultaneously to set a particular current at a given electrode. For example, and returning to the example illustrated in the Background, assume that it is desired to source a current of $53I_{ref}$ at electrode $E_2$. In such an embodiment, any ten of the current sources 410 can be activated via the coarse control signals corresponding to electrode $E_2$ ($C_{X,2}$) to provide $50I_{ref}$ to electrode $E_2$. Likewise, any of three fine current control signals corresponding to electrode $E_2$ ($F_{X,2}$) can be activated to provide an additional $3I_{ref}$ worth of current in addition to the $50I_{ref}$ provided by the coarse portion, resulting in the desired total current of $53I_{ref}$.

Of course, the electrode-dedicated PDACs 409 can provide a fine current resolution using other designs, and the particular design of the PDACs is not critical to embodiments of the invention.

As one skilled in the art will appreciate, it is a matter of design choice as to how many coarse stages L are used, and how many fine stages J are used, and these values may be subject to optimization. However, if it is assumed that J stages are used in the fine portion 403, then the number of stages L used in the coarse portion 402 is preferably equal to $(100/(J+1))-1$. Thus, if J equals 4, the number of stages L will be equal to 19, thereby allowing the coarse portion 402 to supply approximately 95% of the current range to any electrode $E_X$ with a resolution of approximately 5%. In this case, the fine portion 403 supplies approximately the remaining 5% of the current to any electrode $E_X$ at the higher resolution of approximately 1%. However, these values are merely exemplary.

As shown in the Figures, it is preferred to use the same reference current, $I_{ref}$, as the input to the current mirrors 410 in the coarse portion 402 and the PDACs 409 in the fine portion. However, this is not strictly necessary. For example, in FIGS. 12A and 12B, two PDACs 407c and 407f are used to respectively set different reference currents, $I_{ref1}$ and $I_{ref2}$, in the coarse and fine portions 402 and 403. By programming the PDACs 407c and 407f accordingly, these two reference currents can be a scalar of each other (i.e., $I_{ref1}=Q*I_{ref2}$). Assume that $I_{ref1}$ is 5 times the value of $I_{ref2}$ (Q=5). Assume further that only a single output transistor 413 (FIG. 9) is used in the current mirrors 410 in the coarse portion 402. Using these assumptions, the circuitry would operate as discussed earlier: each PDAC 409 in the fine portion 403 outputs a current with a fine resolution, $I_{ref2}$, while each stage in the coarse portion 402 outputs a current with a coarse resolution, $I_{ref1}=5I_{ref2}$. However, in such an embodiment, it would be necessary to isolate the coarse and fine portions 402 and 403 and to provide isolated compliance voltages (power supplies), V1+ and V2+, to each as shown.

Several benefits are had with the new current source/sink architecture of FIGS. 8-13.

Figure 13:
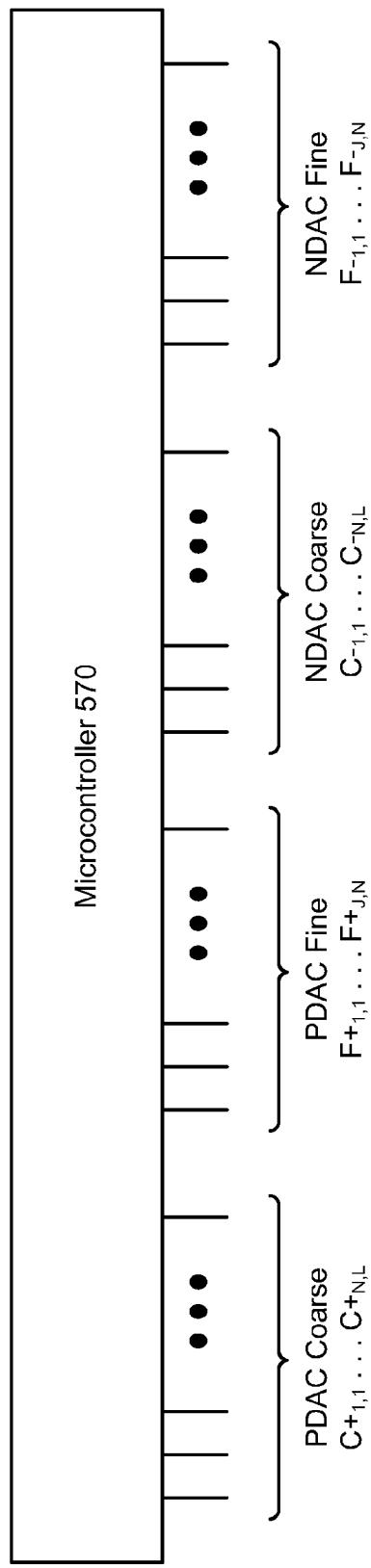
FIG. 13 illustrates the control signals necessary to operate the disclosed embodiment of the current generation circuitry shown in FIGS. 8A and 8B.

First, by splitting the source 400 and sink 401 circuitry into coarse 402 and fine 403 portions, the number of control signals is reduced versus schemes which offer only a unified resolution. The control signals necessary to operate and control the disclosed current source/sink circuitry are shown in FIG. 13. Shown are the coarse ($C_{N,L}$) and fine ($F_{J,N}$) control signals for both the source circuitry (PDACs; designated with a "+") and the sink circuitry (NDACs; designated with a "−"). These control signals are ultimately generated by a microcontroller 570, which can be the microcontroller otherwise used to implement the logic functions in the IPG. Alternatively, the current source/sink circuitry can be implemented on an analog integrated circuit, which receives the control signals from a digital integrated circuit. Again, the specific details concerning the integration of the current source/sink circuitry with the logic can occur in any number of ways, as one skilled in the art will readily recognize.

Second, and unlike the prior art architectures discussed earlier, circuitry is kept to a minimum through reduction of the use of dedicated circuitry which otherwise might be guaranteed to go unused at particular points in time. In large part, this benefit is the result of the distributed nature of the coarse portion 402 of the circuitry across all of the electrodes. While the disclosed design does rely on the use of some dedicated circuitry—specifically, the fine portion 403—such circuitry is preferably kept to a minimum. In any event, such additional dedicated circuitry amounts to a good trade off when it is recognized that this reduces the number of necessary control signals.

Figure 5:
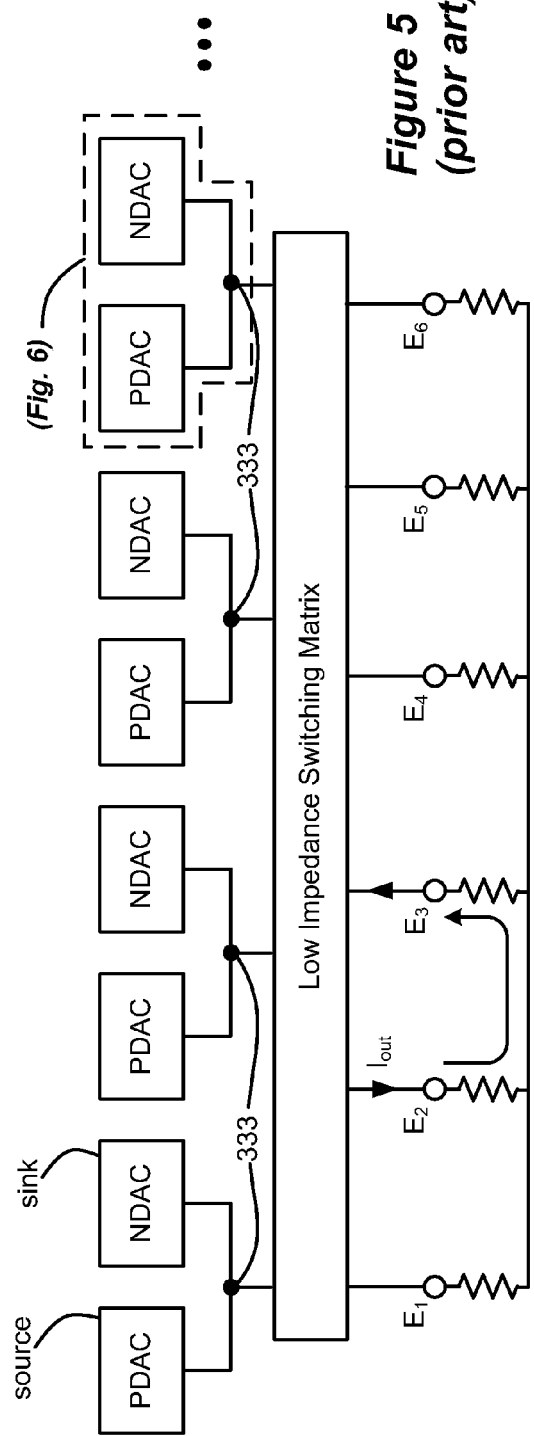
FIG. 5 shows a prior art architecture for coupling current source and sinks to a plurality of electrodes using a switching matrix.
Figure 6:
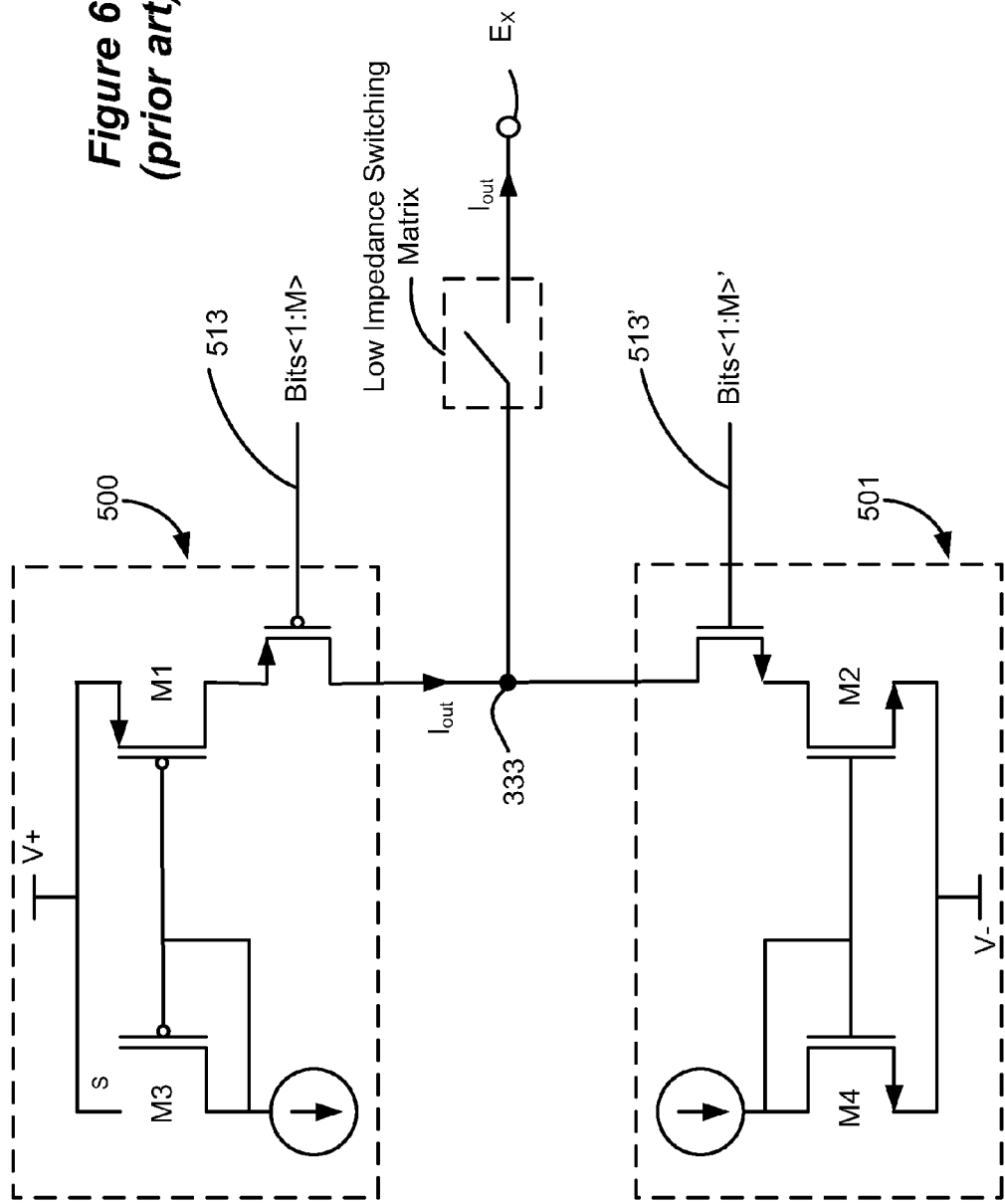
FIG. 6 shows drawbacks relating to the architecture of FIG. 5 relating to unnecessary power consumption within the IPG.

Third, as compared to the prior art switch matrix approach of FIGS. 5 and 6, the new architectures of FIGS. 8-12 comprise one less component in the output path, which reduces unwanted voltage drops in the output path and results in power savings. As can be seen with brief reference to FIGS. 9 and 10, which shows the circuitry in the coarse portion 402, only two components intervene between the power supply V+ and a given electrode: the current mirror output transistor(s) 413 and the selection switches 417 from the switch banks 405. Moreover, as concerns the fine portion 403, shown in FIG. 11, again only two components intervene between the power supply V+ and a given electrode: the current mirror output transistors 422 and the selection switches 431. In addition to reducing the series resistance in the circuit by eliminating the series switch matrix, the selection switches 417 linearize the current sources 410 by reducing the Vds voltage drop across the current mirrors on electrodes that require less compliance voltage than the difference of V+ to V−. If it were not for the switches 417, the entire excess compliance drop would be across the current mirror 410 and the current would tend to be a little higher than programmed on electrodes requiring less compliance voltage.

It should be understood that the direction in which current flows is a relative concept, and different conventions can be used to define whether currents flow to or from various sources. In this regard, arrows showing the directions of current flows in the Figures, references to current flowing to or form various circuit nodes, references to currents being sunk or sourced, etc., should all be understood as relative and not in any limiting sense.

It should also be understood that reference to an electrode implantable adjacent to tissue to be stimulated includes electrodes on the implantable stimulator device, or associated electrode leads, or any other structure for stimulating tissue.

Figure 7:
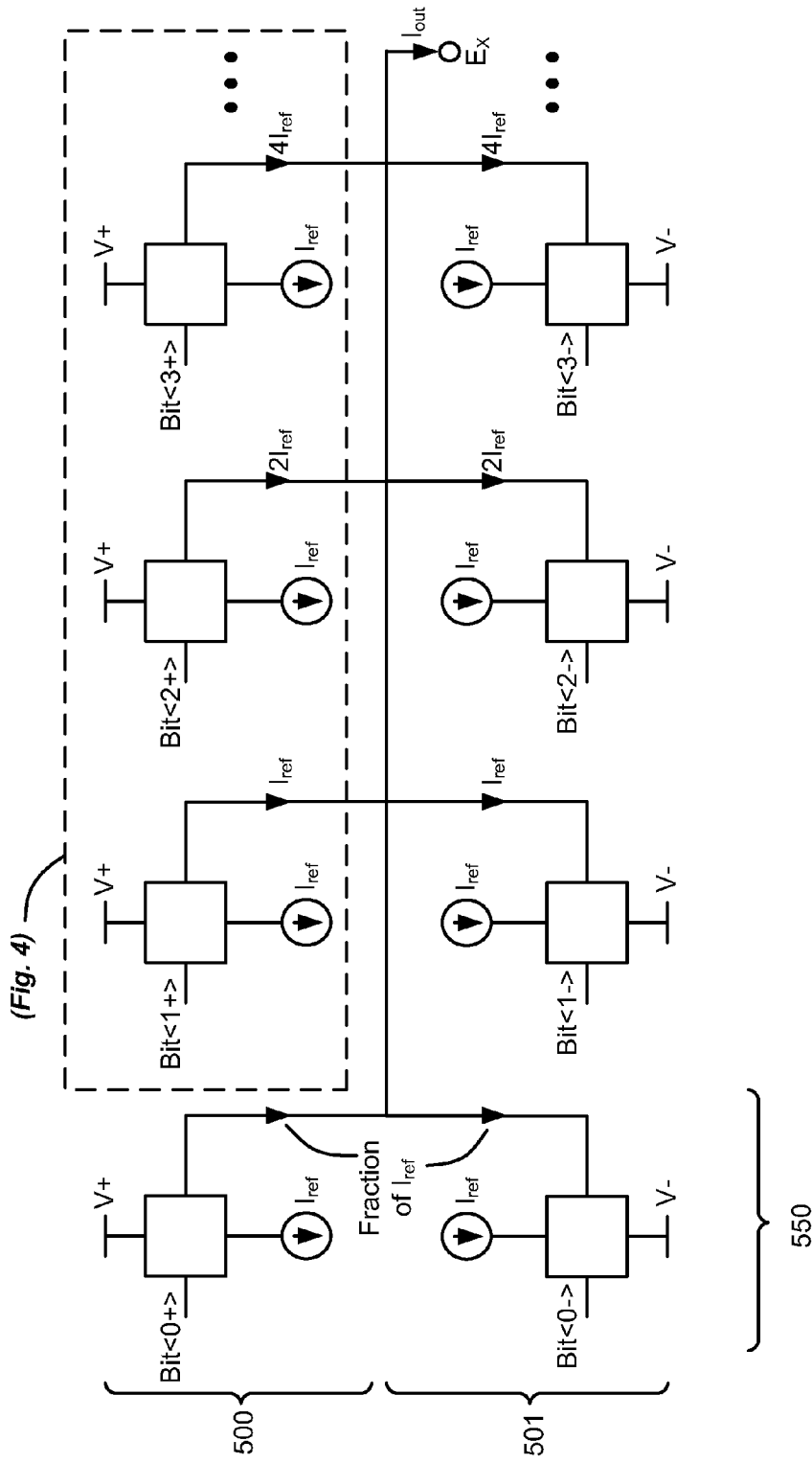
FIG. 7 shows a prior art modification to the architecture of FIGS. 3 and 4 in which a fractional amount of a reference current can be provided at an electrode.

Moreover, it should be understood that an electrode implantable adjacent to tissue to be stimulated is to be understood without regard to any output capacitance, such as coupling capacitances $C_N$ included in the header connector 192 or elsewhere (see FIG. 7). This is so because it should be understood that nodes on both sides of such a coupling capacitor or other output impedance are, in the context of this invention, not materially different from an architectural standpoint, such that either node would be considered as the electrode node implantable adjacent to tissue to be stimulated. The same would be true for other impedances, e.g., if an output resistor was used in addition to or in lieu of a coupling capacitor.

While the invention herein disclosed has been described by means of specific embodiments and applications thereof, numerous modifications and variations could be made thereto by those skilled in the art without departing from the literal and equivalent scope of the invention set forth in the claims.

What is claimed is:

1. An implantable stimulator, comprising:
a plurality of electrode nodes;
a processor; and
a stimulation generator coupled to the processor and the electrode nodes, the stimulation generator comprising:
a plurality of negative electrical sources that are each directly connected to a different one of the plurality of electrode nodes;
a switching unit that is connected to each of the plurality of electrode nodes; and
at least one positive electrical source connected to the switching unit,
wherein the switching unit is configured to connect the at least one positive electrical source to a selected one or more of the plurality of electrode nodes.

2. The implantable stimulator of claim 1, wherein the processor controls the switching unit to connect the at least one positive electrical source to the selected one or more of the plurality of electrode nodes.

3. The implantable stimulator of claim 1, wherein one of the plurality of negative electrical sources is directly connected to a first electrode node in the plurality of electrode nodes, and wherein the switching unit is configured to connect the at least one positive electrical source to a second electrode node in the plurality of electrode nodes, such that a first electrode connected to the first electrode node comprises a cathode and a second electrode connected to the second electrode node comprises an anode.

4. The implantable stimulator of claim 1, wherein the at least one positive electrical source comprises a plurality of positive electrical sources that are each connected to the switching unit, and wherein the switching unit is configured to connect each of the plurality of positive electrical sources to a selected one of the plurality of electrode nodes.

5. The implantable stimulator of claim 1, wherein the stimulation generator further comprises:
a second plurality of negative electrical sources that are each directly connected to a different one of a second plurality of electrode nodes;
a second switching unit that is connected to the second plurality of electrode nodes; and
at least one additional positive electrical source connected to the second switching unit,
wherein the second switching unit is configured to connect the at least one additional positive electrical source to a selected one or more of the second plurality of electrode nodes.

6. The implantable stimulator of claim 1, further comprising at least one lead that includes a plurality of electrodes, each of the electrodes connected to a respective one of the plurality of electrode nodes.

7. The implantable stimulator of claim 1, wherein the switching unit comprises at least one multiplexer.

8. The implantable stimulator of claim 1, wherein the stimulation generator comprises a pulse generator, and wherein the plurality of negative electrical sources and the at least one positive electrical source are each selected from a group consisting of a current source and a voltage source.

9. A stimulation generator, comprising:
a plurality of negative electrical sources that are each directly connected to a different one of a plurality of electrode nodes that are coupled to the stimulation generator;
a switching unit that is connected to each of the plurality of electrode nodes; and
at least one positive electrical source connected to the switching unit,
wherein the switching unit is configured to connect the at least one positive electrical source to a selected one or more of the plurality of electrode nodes.

10. The stimulation generator of claim 9, wherein one of the plurality of negative electrical sources is directly connected to a first electrode nodes in the plurality of electrode nodes, and wherein the switching unit is configured to connect the at least one positive electrical source to an electrode nodes in the plurality of electrode nodes, such that a first electrode connected to the first electrode node comprises a cathode and a second electrode connected to the second electrode node comprises an anode.

11. The stimulation generator of claim 9, wherein the at least one positive electrical source comprises a plurality of positive electrical sources that are each connected to the switching unit, and wherein the switching unit is configured to connect each of the plurality of positive electrical sources to a selected one of the plurality of electrode nodes.

12. The stimulation generator of claim 9, wherein the stimulation generator further comprises:
- a second plurality of negative electrical sources that are each directly connected to a different one of a second plurality of electrode nodes;
- a second switching unit that is connected to the second plurality of electrode nodes; and
- at least one additional positive electrical source connected to the second switching unit,
- wherein the second switching unit is configured to connect the at least one additional positive electrical source to a selected one or more of the second plurality of electrode nodes.

13. The stimulation generator of claim 9, wherein the switching unit comprises at least one multiplexer.

14. The stimulation generator of claim 9, wherein the stimulation generator comprises a pulse generator, and wherein the plurality of negative electrical sources and the at least one positive electrical source are each selected from a group consisting of a current source and a voltage source.

15. A method, comprising:
- directly connecting each of a plurality of negative electrical sources in a stimulation generator to a different one of a plurality of electrode nodes;
- connecting a switching unit in the stimulation generator to each of the plurality of electrode nodes; and
- connecting at least one positive electrical source in the stimulation generator to the switching unit.

16. The method of claim 15, further comprising:
- directly connecting each of a second plurality of negative electrical sources in the stimulation generator to a different one of a second plurality of electrode nodes;
- connecting a second switching unit in the stimulation generator to each of the second plurality of electrode nodes; and
- connecting at least one additional positive electrical source in the stimulation generator to the second switching unit.

17. The method of claim 15, wherein the switching unit comprises at least one multiplexer.

18. The method of claim 15, wherein the stimulation generator comprises a pulse generator, and wherein the plurality of negative electrical sources and the at least one positive electrical source are each selected from a group consisting of a current source and a voltage source.

19. A method, comprising:
- using an electrode node combination for an implantable stimulator that includes a first set of one or more electrode nodes that are each connected to an anode, wherein the electrode node combination further includes a second set of one or more electrode nodes that are each connected to a cathode;
- configuring a switching unit in a stimulation generator to connect at least one positive electrical source in the stimulation generator to the first set of one or more electrode nodes;
- activating the at least one positive electrical source; and
- activating at least one negative electrical source in the stimulation generator, wherein the at least one negative electrical source is directly connected to the second set of one or more electrode nodes.

20. The method of claim 19, further comprising deactivating at least one additional negative electrical source that is connected to the first set of one or more electrode nodes.

21. The method of claim 19, wherein the at least one positive electrical source comprises a plurality of positive electrical sources, wherein the first set of one or more electrode nodes comprises a first plurality of electrode nodes, and wherein the method comprises configuring the switching unit to connect each of the plurality of positive electrical sources to a selected one of the first plurality of electrode nodes.

22. The method of claim 19, further comprising:
- using a second electrode node combination for the implantable stimulator that includes a third set of one or more electrode nodes that are each connected to an anode, wherein the second electrode node combination further includes a fourth set of one or more electrode nodes that are each connected to a cathode;
- configuring a second switching unit in the stimulation generator to connect at least one additional positive electrical source in the stimulation generator to the third set of one or more electrode nodes;
- activating the at least one additional positive electrical source; and
- activating at least one additional negative electrical source in the stimulation generator, wherein the at least one additional negative electrical source is directly connected to the fourth set of one or more electrode nodes.

23. The method of claim 19, wherein the switching unit comprises at least one multiplexer.

24. The method of claim 19, wherein the stimulation generator comprises a pulse generator, and wherein the at least one negative electrical source and the at least one positive electrical source are each selected from a group consisting of a current source and a voltage source.

25. An apparatus, comprising:
- means for using an electrode node combination for an implantable stimulator that includes a first set of one or more electrode nodes that are each connected to an anode, wherein the electrode node combination further includes a second set of one or more electrode nodes that are each connected to a cathode;
- means for configuring a switching unit in a stimulation generator to connect at least one positive electrical source in the stimulation generator to the first set of one or more electrode nodes;
- means for activating the at least one positive electrical source; and
- means for activating at least one negative electrical source in the stimulation generator, wherein the at least one negative electrical source is connected to the second set of one or more electrode nodes.

* * * * *